(12) United States Patent
Gögler

(10) Patent No.: US 9,664,599 B2
(45) Date of Patent: May 30, 2017

(54) LASER MICRODISSECTION METHOD AND LASER MICRODISSECTION DEVICE

(75) Inventor: Michael Gögler, Munich (DE)

(73) Assignee: CARL ZEISS MICROSCOPY GMBH, Jena (DE)

( * ) Notice: Subject to any disclaimer, the term of this patent is extended or adjusted under 35 U.S.C. 154(b) by 890 days.

(21) Appl. No.: 14/005,575

(22) PCT Filed: Mar. 21, 2012

(86) PCT No.: PCT/EP2012/055034
§ 371 (c)(1),
(2), (4) Date: Nov. 25, 2013

(87) PCT Pub. No.: WO2012/126961
PCT Pub. Date: Sep. 27, 2012

(65) Prior Publication Data
US 2014/0190946 A1    Jul. 10, 2014

(30) Foreign Application Priority Data
Mar. 22, 2011 (DE) ........................ 10 2011 001 474

(51) Int. Cl.
*B23K 26/38* (2014.01)
*B23K 26/40* (2014.01)
*G01N 1/28* (2006.01)
*B23K 26/00* (2014.01)
*B23K 103/00* (2006.01)

(52) U.S. Cl.
CPC ......... *G01N 1/286* (2013.01); *B23K 26/0006* (2013.01); *B23K 26/38* (2013.01); *B23K 2203/30* (2015.10); *G01N 2001/2886* (2013.01); *G05B 2219/45041* (2013.01)

(58) Field of Classification Search
CPC .............. B23K 26/032; B23K 26/0626; G05B 2219/45041; G01N 1/286; G01N 2001/2886
See application file for complete search history.

(56) References Cited

U.S. PATENT DOCUMENTS 4,670,639 A * 6/1987 Behn .................. B23K 26/0736
219/121.69
4,734,550 A * 3/1988 Imamura ............ B23K 26/0732
219/121.61

(Continued)

FOREIGN PATENT DOCUMENTS

DE    102007035582 A1    2/2009
DE    102005028062 B4    11/2010

(Continued)

OTHER PUBLICATIONS

Author Unknown, "Software Manual," PALM RoboSoftware; Microlaser Systems; Version 3.0-0804 (EN); Aug. 2004. pp. 89-146.

*Primary Examiner* — Geoffrey S Evans
(74) *Attorney, Agent, or Firm* — Murphy, Bilak & Homiller, PLLC

(57) ABSTRACT

Methods and apparatuses for laser microdissection are provided. For example, by a user at least one first system parameter is adjusted, for example varied, and at least one second system parameter of the laser microdissection system is adjusted automatically by the laser microdissection system such that a cut line has a desired cut line parameter.

19 Claims, 4 Drawing Sheets

(56) References Cited

U.S. PATENT DOCUMENTS

| | | | | |
|---|---|---|---|---|
| 5,012,069 A | * | 4/1991 | Arai | B23K 26/0853 |
| | | | | 219/121.62 |
| 5,589,090 A | * | 12/1996 | Song | B23K 26/032 |
| | | | | 219/121.62 |
| 6,031,200 A | * | 2/2000 | Whitehouse | G01B 11/02 |
| | | | | 219/121.67 |
| 6,786,713 B2 | * | 9/2004 | Fukushima | B22F 3/03 |
| | | | | 264/177.12 |
| 2002/0164678 A1 | * | 11/2002 | Ganser | G01N 1/04 |
| | | | | 435/40.5 |
| 2005/0155954 A1 | * | 7/2005 | Oba | B28D 5/023 |
| | | | | 219/121.67 |
| 2006/0289411 A1 | * | 12/2006 | Chang | B23K 26/0622 |
| | | | | 219/121.73 |
| 2007/0215581 A1 | * | 9/2007 | Kato | B28D 1/221 |
| | | | | 219/121.69 |
| 2008/0194011 A1 | | 8/2008 | Wesner | |
| 2010/0084386 A1 | * | 4/2010 | Masuda | B23K 26/066 |
| | | | | 219/121.67 |
| 2010/0090108 A1 | | 4/2010 | Hoeche | |
| 2011/0100966 A1 | * | 5/2011 | Nagatomo | B23K 26/0087 |
| | | | | 219/121.72 |
| 2011/0220623 A1 | * | 9/2011 | Beutler | B23K 26/0876 |
| | | | | 219/121.67 |
| 2012/0145686 A1 | * | 6/2012 | Alpay | B23K 26/0734 |
| | | | | 219/121.67 |

FOREIGN PATENT DOCUMENTS

| | | | |
|---|---|---|---|
| EP | 1985987 A2 | | 10/2008 |
| EP | 2169491 A1 | * | 3/2010 |
| JP | 56-165583 A | * | 12/1981 |
| JP | 03-155484 A | * | 7/1991 |
| JP | 06-000673 A | * | 1/1994 |
| JP | 2000-351087 A | * | 12/2000 |
| WO | 0173398 A1 | | 10/2001 |
| WO | 03036266 A1 | | 5/2003 |
| WO | 03060477 A2 | | 7/2003 |
| WO | 2005033669 A1 | | 4/2005 |
| WO | WO-2005/033669 A1 | * | 4/2005 |
| WO | WO-2009/007708 A2 | * | 1/2009 |
| WO | WO-2010/028514 A1 | * | 3/2010 |

* cited by examiner

LASER MICRODISSECTION METHOD AND LASER MICRODISSECTION DEVICE

TECHNICAL FIELD

The present application relates to methods and apparatuses for laser microdissection.

BACKGROUND

Laser microdissection systems are often employed for processing, separating and/or obtaining of biological objects, in particular microscopically small objects.

There, areas of interest of a sample are cut out by means of the laser beam, for example a pulsed laser beam. The sample may be provided on a carrier, for example a sheet, which has a high absorption for the laser light used.

Optionally the cut-out area may be transported to a receiving container via laser-induced transport process. Properties of a cut line of such a cutting process, for example width of the cut line or freeness from interruptions of the cut lines depend on system parameters which are partially adjustable, for example laser parameters like a laser energy or a repetition rate of a pulsed laser or also other system parameters like a focus adjustment or a cutting speed caused by a movement of the object and/or of the laser beam. As different biological samples have different properties it is often necessary to adjust the system parameters for each sample or also for each series of similar samples. In this respect from applicant's EP 1 985 987 A2 a generic laser microdissection apparatus is known with which finding suitable systems parameters is facilitated by using a reference cut line.

However, it may occur that a user wants to change one of the parameters after finding a suitable combination of systems parameters. For example it is often easier to find suitable parameters with a low cutting speed. For the actual processing of samples for time reasons often a fast cutting speed is desirable or necessary. Conventionally, in such a case one or more system parameters have to be adjusted anew.

Therefore, there is a need for methods and apparatuses for laser microdissection in which the adjustment and/or changing of suitable system parameters is facilitated.

SUMMARY

According to an embodiment, a method for laser microdissection comprises:

Adjusting at least one first system parameter of a laser microdissection system, for example by a user, and automatically adjusting of at least one second system parameter depending on the at least one first system parameter of the laser microdissection system such that a desired value of a cut line parameter describing a cut line of the laser microdissection system is present.

By automatically adjusting the at least one second system parameter in such an embodiment a finding of suitable system parameters is facilitated. The automatically adjusting may take place in response to a request of a user or also without further action of a user. The desired value may be a predetermined value or a value within a predetermined range, for example a range predetermined by a user and/or by system properties (for example tolerances).

System parameters generally are parameters which directly relate to the adjusting of components of the laser microdissection system. Examples of these are laser parameters like laser energy or laser repetition rate of pulsed lasers, cutting speed for example through movement of a sample holder or a movement of the laser beam, focus of a laser beam, aperture of a laser beam or the profile, i.e. lateral intensity distribution, or beam form of a laser beam. Cut line parameters in contrast thereto are parameters, which describe a cut line generated with a specific setting of the systems parameters, for example a parameter designating the cut width or a parameter which indicates whether the cut line is free of interruptions. The desired cut line parameter may therefore for example indicate that an interruption-free cut is executed.

In an embodiment adjusting the at least one first parameter comprises varying the at least one first system parameter starting from a previously set value. In this case the automatically adjusting of the at least one second system parameter may take place such that the desired value of the cut line parameter is at least approximately kept constant, for example within a predetermined range, for example a range predetermined by a user and/or by system properties like tolerances or possible values of the system parameter. In other words the keeping constant may be performed as far as possible given system constrains. The previously set value may for example be a value set by a user.

To achieve this in particular it may be used that cut line parameters at least in part depend on a plurality of system parameters and therefore changes of the at least one first system parameter may be compensated by changes of the at least one second system parameter. In this way for example cutting speed and laser energy, repetition rate and laser energy, cutting speed and repetition rate and/or position of a laser focus and laser energy may mutually compensate each other.

For the automatically adjusting relationships between the system parameters may be used which for example may be stored in a memory.

A laser microdissection apparatus according to an embodiment comprises a laser device for generating a laser beam, a receptacle, for example a microscope table, for receiving a sample to be examined and a control device for controlling the laser microdissection apparatus. Furthermore the apparatus according to the invention may comprise a user interface. The laser microdissection apparatus, in particular the control device, is configured to execute one of the methods according to embodiments described above.

The above-described features and variants may be combined with each other unless noted otherwise.

The above summary is not to be construed as limiting, but is merely intended to give an overview over some features of some embodiments.

BRIEF DESCRIPTION OF THE DRAWINGS

In the following the invention will be explained in more detail referring to the attached drawings using embodiments.

DETAILED DESCRIPTION

In the following embodiments of the present invention will be discussed in more detail. In this respect in FIG. 1 a laser microdissection system according to an embodiment is shown. The embodiment shown has a so called inverse configuration in which a sample is irradiated by a laser beam from below. The disclosed techniques, however, are equally applicable to upright, i.e. non-inverse, configurations, in which irradiation with a laser beam takes place from above.

Figure 1:
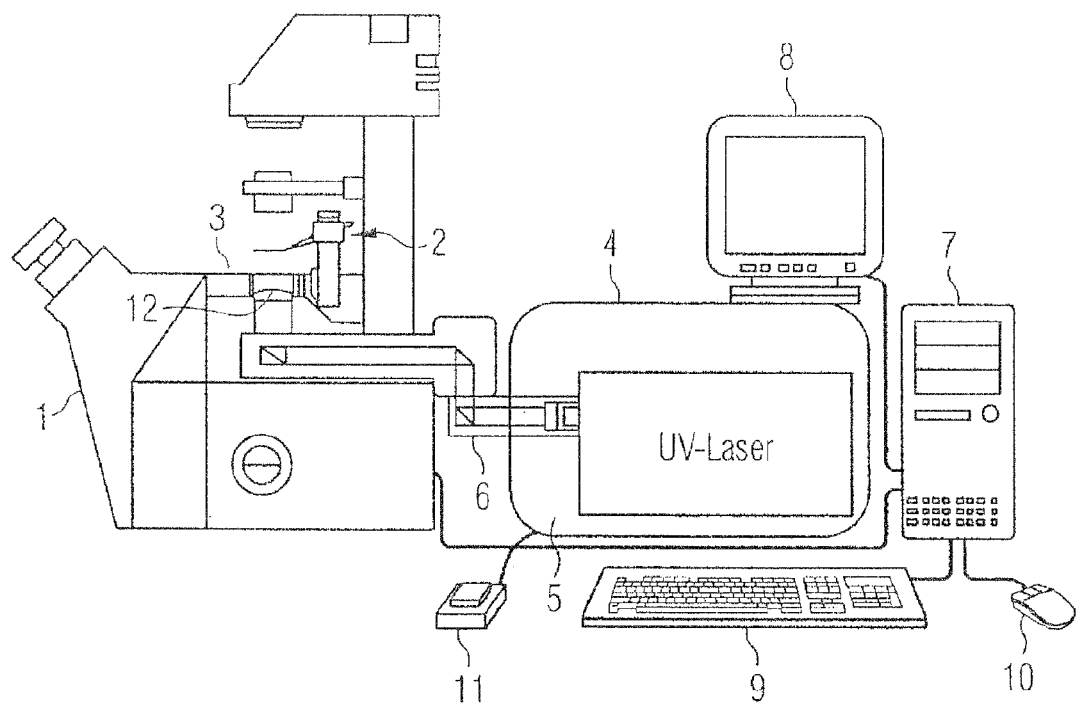
FIG. 1 shows an embodiment of an apparatus.

The laser microdissection system shown in FIG. 1 comprises a laser device 4 in which a laser light source for generating a laser beam is accommodated. Furthermore in laser device 4 an optic 6 is accommodated via which a laser beam is coupled into a microscope 1 and with the help of which the laser focus may be displaced in the object plane with respect to the optical focus of microscope 1. In other words, via optic 6 a focus of the laser beam generated by laser device 4 is adjustable independently of a focus of microscope 1. For changing the focus of the laser beam for example lenses of optic 6 may be moved via a stepper motor. The laser light source may for example be a pulsed UV nitrogen laser, for example having a wavelength of 337 nm, the energy of a laser pulse may be of the order of 100-500 µJ, a pulse duration may be of the order of 3 ms and a repetition rate, i.e. a pulse frequency, may be 1-30 Hz. It is to be noted that the above numerical values are merely to be understood as an example. In the embodiment shown the pulse energy and/or the repetition rate is adjustable. Also other laser light sources than nitrogen lasers may be used, for example a solid state laser with a frequency multiplier, for example a solid state laser with a frequency tripler and a resulting wavelength of 355 nm. Such solid state lasers typically have an energy between 1 and 200 µJ, a pulse duration of about 1 ms and an adjustable repetition rate between 1 and 10000 Hz.

Additionally or alternatively to the adjustment of the pulse energy via the laser light source itself in the embodiment of FIG. 1 a quartz filter 5 is positioned perpendicular to a laser light path, which quartz filter may be automatically or also manually adjusted to change the laser energy.

In the embodiment shown in FIG. 1, the laser beam is coupled into microscope 1 via a plurality of optical elements, for example mirrors, and guided to an objective lens 12. The diameter of the laser beam in an object plane is depending inter alia on the numerical aperture of objective lens 12, an objective lens with a comparatively high numerical aperture enabling laser beam diameters of for example smaller than 1 µm.

The laser light source of laser device 4 in an embodiment may comprise an adjustable aperture via which an aperture of the laser light source is adjustable.

The laser beam emitted via objective lens 12 reaches a motorized and automatically controllable microscope table or carrier table 3 which serves as a receptacle for a sample. For example a carrier with a biologic material to be processed, i.e. a biologic object, may be provided on carrier table 3. Optionally, above carrier table 3 a preferably also motorized and automatically controllable manipulator 2 is provided, wherein both carrier tables 3 and manipulator 2 may also be manually adjustable. The components 2 and 3 enable an exact positioning of an object with high precision as well as a computer-based fully automatic performance of micro-manipulation procedures.

The motorized carrier table 3 is displaceable at least in the x/y-plane, i.e. in the plane of the carrier table. Manipulator 2 may be displaced both in x/y direction and in z-direction, i.e. perpendicular to carrier table 3. A needle or a micropipette 4 performing a microinjection may be mounted to manipulator 2, for example. Also, a catching device may be mounted to manipulator 2 to catch removed areas of biologic objects coming from the carrier. Manipulator 2 may therefore serve in particular as holding device for components like a needle, a micropipette or a catching device.

Microscope 1 may be an arbitrarily designed microscope. In particular, both the use of an inverse and of an upright microscope or of a laser microscope is imaginable. Microscope 1 shown in FIG. 1 is an inverse microscope in which the laser beam falls on carrier table 3 from below to cut biologic objects disposed thereon and possibly transfer them with a laser induced transfer process to a catching device present at manipulator 2. In an upright configuration, in contrast thereto the laser beam falls on the carrier from above, such that for example parts cut out of a biologic object may fall downwards on a catching device present below carrier table 3 or may be transported there, respectively.

Microscope 1 may be provided with an image capturing unit (not explicitly shown), in particular in the form of an image sensor like a CCD-sensor ("charged coupled device") or CMOS ("complementary metal oxide semiconductor") sensor, which may capture a biologic object present on carrier 3. The signal of such an image capturing unit is fed to a computer 7 and processed there such that a corresponding video image may be displayed in real time on a display 8 of computer 7. Additionally or alternatively, microscope 1 may be configured for direct visual control of the biologic object present on carrier table 3. Individual captured images may be stored on a suitable storage medium using computer 7.

Computer 7 or one or more microprocessors contained therein, respectively, in conjunction with software running on the computer in the embodiment of FIG. 1 serves as control device of different functions of the laser microdissection system. The software may be loaded via an exchangeable data carrier like a CD ROM, a DVD ROM or a chip card into computer 7 or may as well be present on a hard disk or a fixedly integrated storage medium in computer 7. It is to be noted that instead of computer 7 also other kinds of control devices are possible, for example control devices with microprocessors and fixed programs contained for example in a read only memory (ROM).

The control device realized with the aid of computer 7 allows in particular an automatic control of laser device 3, carrier table 3, manipulator 2 and/or microscope 1, such that for example system parameters like laser parameters may be adjusted or set and manipulator 2 or carrier table 3, respectively, may be automatically displaced. System parameters are to be understood as parameters which directly influence the function of components of the system of FIG. 1. Examples for system parameters are laser parameters as for example a pulse energy of the used laser light source or a repetition rate of the laser light source as well as further system parameters like a focus position of the laser beam or a speed with which carrier table 3 moves.

Furthermore, the control device may enable a selection and a processing of desired biologic objects which are present on carrier table 3. For setting or selection, respectively, of diverse functions of the control device in the embodiment of FIG. 1 input means like for example a keyboard 9 and a mouse 10 are provided. Furthermore, a foot switch 11 is associates with laser device 4 in the embodiment shown in FIG. 1 through the actuation of which the laser may be actuated manually. Keyboard 9, mouse 10 and foot switch 11 together with display 8 form an example for a user interface of the laser microdissection apparatus. However, also other means for inputting and outputting data by or to a user, respectively, are possible, for example so-called joysticks, displays with individual light emitting diodes and/or acoustic signals.

By means of the laser microdissection apparatus of FIG. 1 in particular areas of biologic or also other objects may be cut out, i.e. a laser microdissection may be performed. For this example a desired cut line may be given by a user for example by means of mouse 10 on display 8, and also desired system parameters for carrying out the cut may be given. Following this by the apparatus of FIG. 1 an automatic performance of the cut may take place. Further functions which may be performed by means of the laser microdissection system of FIG. 1 are for example described in detail in EP 1 985 987 A2 mentioned in the introduction or also in WO 03/036266 A1 and WO 01/73398 A1 of the applicant such that these conventional functions of a laser microdissection system are not again explained in detail here.

For performing such a cut then carrier table 3 may be moved such that the laser beam which in this case is stationary runs along the corresponding cut line. In other embodiments, additionally or alternatively also the laser beam may be moved on the biologic object, for example by corresponding movable mirrors, prisms or by holographic techniques like spatial light modulators.

Figure 2:
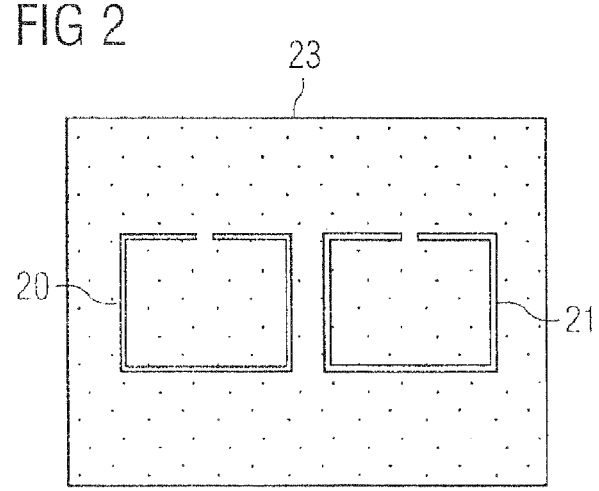
FIG. 2 shows examples for different cut lines.

Different system parameters thereby may cause different forms of a resulting cut line. A simple example for this is shown in FIG. 2. In particular in FIG. 2 a biologic object 23 is shown in which two cut lines 20, 21 were cut. Cut line 20 was cut with a lower pulse energy, a lower repetition rate and/or a higher cutting speed than cut line 21 which leads to a wider cut line 21.

The biologic object in particular may be disposed on a carrier sheet or membrane which has a high absorption for the laser radiation used.

At an even lower repetition rate or laser energy or an even higher cutting speed, respectively, than used for cut line 20 interruptions of the cut line may occur.

Parameters which describe form and appearance of a cut line in the following will be referred to as cut line parameters, as already mentioned. For example the width of a cut line is such a cut line parameter. Another cut line parameter may for example indicate if the cut line is free of interruptions or not, and therefore may be a parameter with only two possible values. The cut line parameters therefore depend on the above-described system parameters.

To find suitable system parameters for a biologic object to be treated for example test cuts may be performed as described in EP 1 985 987 A2 which are then compared to reference cuts. Also, a completely manual setting of such cut line parameters is possible. For this it is for example helpful to select a relatively low cutting speed, i.e. for example a small displacement speed of carrier table 3, as then the adjustment is facilitated. On the other hand, for the actual treatment of biologic objects for time reasons it may be advantageous to select a higher cutting speed, the cutting speed as explained above influencing the cut line parameters.

In an embodiment of the invention, the control device of the laser microdissection system, for example computer 7 of FIG. 1, provides functions which upon a change of a system parameter, for example the cutting speed, adjust other system parameters automatically to keep cut line parameters as constant as possible, for example at values which correspond to an initial setting of the system parameters. A corresponding method according to an embodiment which may be implemented on computer 7 of FIG. 1 and in particular may be integrated in a corresponding control software will now be explained in more detail with reference to FIG. 3.

Figure 3:
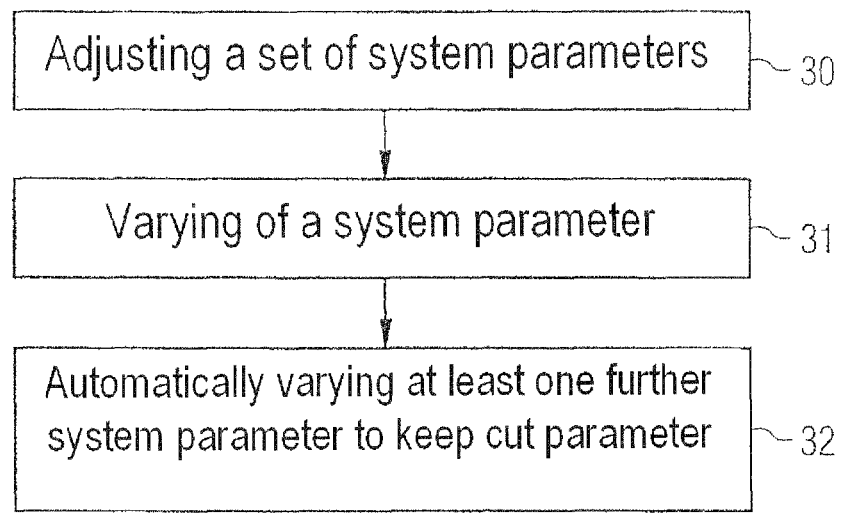
FIG. 3 shows a flow chart of a method according to an embodiment.

In a step 30 of the method of FIG. 3 a set of system parameters is adjusted. This may for example fully or partially be done by a user of a laser microdissection system. For this, for example test cuts on a biologic object may be performed and the system parameters may be varied such that desired cut line parameters, for example an interruption-free cut and/or a desired cut width, for example within a desired range, are obtained. As already mentioned this adjustment of the set of system parameters may also take place supported by the system, i.e. at least semi-automatic.

When a set of system parameters is found which leads to a desired quality of the cut line, i.e. to desired cut line parameters, a user may input that now the cut line parameters correspond to the desired ones. For example, this may take place by a corresponding input via keyboard 9 or mouse 10 of FIG. 1, for example by clicking a certain field on display 8 by means of mouse 10. It is equally possible, however, to determine an initial set of system parameters automatically, for example such that at a given cutting speed a cut without interruptions is present.

In a step 31, then a system parameter is varied. For example a cutting speed, for example a speed of a movement of carrier table 3 of FIG. 1, may be increased.

In step 32, then at least one further system parameter is automatically varied to keep one or more cut line parameters obtained in step 13 at least approximately constant, for example within a predetermined range. For this as will be explained later with reference to FIGS. 5-8 in more detail stored mutual dependencies between the system parameters may be used. For example upon an increase of the cutting speed a pulse energy and/or a repetition rate of a used laser may be increased.

In this way for example the adjustment of a set of system parameters in step 30 may take place using a slow cutting speed, while then after the varying in step 31 the actual treatment of the biologic object may take place with a higher cutting speed, whereby one or more desired cut line parameters, for example an interruption freeness of the cut line, are maintained. It is to be noted that in step 31 also other system parameters than the cutting speed may be changed, for example a pulse energy or a repetition rate of the laser.

Figure 4:
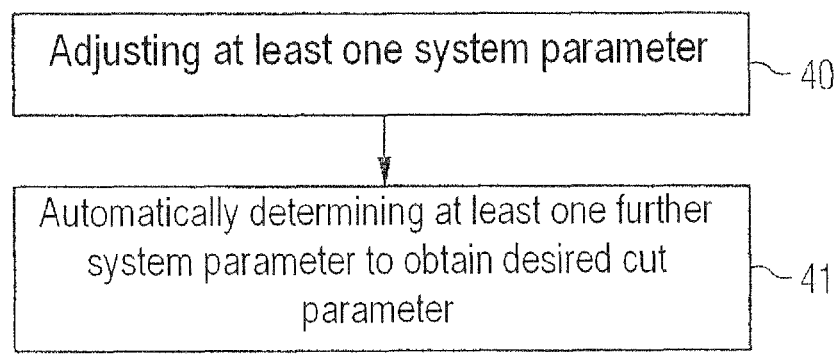
FIG. 4 shows a flow chart of an apparatus according to a further embodiment.

A further method according to an embodiment which may be implemented in a controller of a laser microdissection apparatus, for example in computer 7 of FIG. 1, additionally or alternatively to the method of FIG. 3 is shown in FIG. 4.

In a step 40, at least one system parameter is adjusted. This may for example be performed by a user. For example, a user may input a desired energy and pulse rate.

In step 41, at least one further system parameter, for example all system parameters not set in step 40, are computed, to obtain a desired cut line parameter. In the above example in which in step 40 energy and pulse rate are given for example then in step 41 a suitable cutting speed may be automatically set, for example to obtain an interruption-free cut and/or to obtain a desired cut width. Also, for these stored relationships between the various system parameters may be used to perform the automatic determination.

Such relationships between system parameters may for example be determined experimentally and then stored for different desired cut line parameters and/or for different kinds of biologic objects or other samples and/or for different types of carriers, for example for different types of laser absorbing sheet carriers. Between different recorded measurement points an interpolation may be performed. Some examples for such measurements which correspond to a calibration of the laser microdissection apparatus for application of the above-described methods according to the invention in the following will be described with reference to FIGS. 5-8. Such a calibration may for example be performed by a manufacturer, it may, however, also be performed by a user of laser microdissection system.

Figure 5:
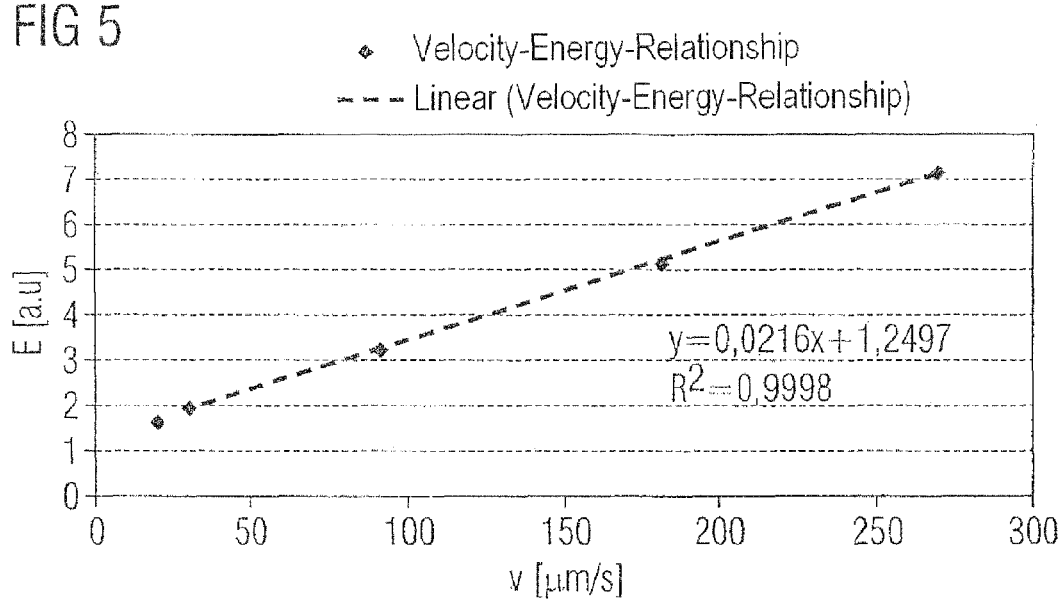
FIGS. 5-8 show examples for relationships between different system parameters.

In FIG. 5 a relationship between pulse energy and cutting speed is shown. In FIG. 5 individual measurement points and also with a dashed a linear fit of the form E=a·v+b are shown, E being the energy, v the speed and a and b fitting parameters. For the measurement the cutting speed has been varied and then the pulse energy was adjusted such that the cut was just free of interruptions, i.e. a cut line parameter which indicated freeness from interruptions having been kept constant.

In this case for example the parameters a and b may be stored to for example in the embodiment of FIG. 5 adjust the pulse energy in step 32 accordingly upon a variation of the cutting speed in step 31.

Figure 6:
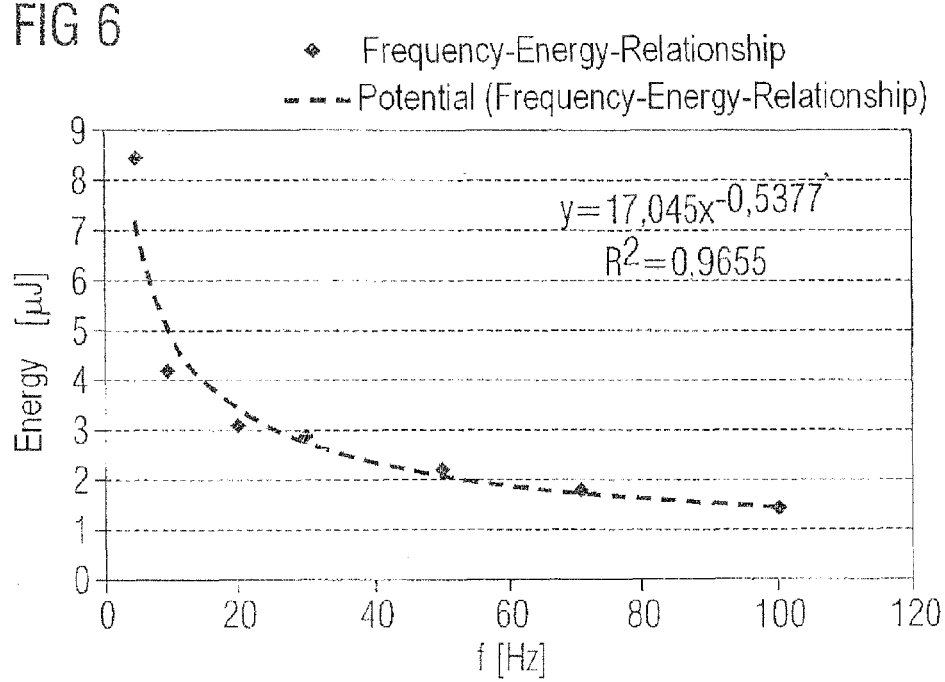

In FIG. 6 a relationship between pulse rate and energy is shown, the energy being given in μJ and the pulse rate being given in Hz. For recording the measurement the cutting speed was kept constant, the pulse rate of the UV-laser used was varied and the pulse energy was adjusted such an interruption-free cut was present, in this case on a carrier sheet, in particular a PEN-sheet. A relationship of the form $E=a \cdot f^{-b}$ results, E being the energy, f the pulse rate and a and b again being parameters. Like in the example of FIG. 5 corresponding parameters may be stored and used for example in embodiments of FIGS. 1, 3 and 4.

Figure 7:
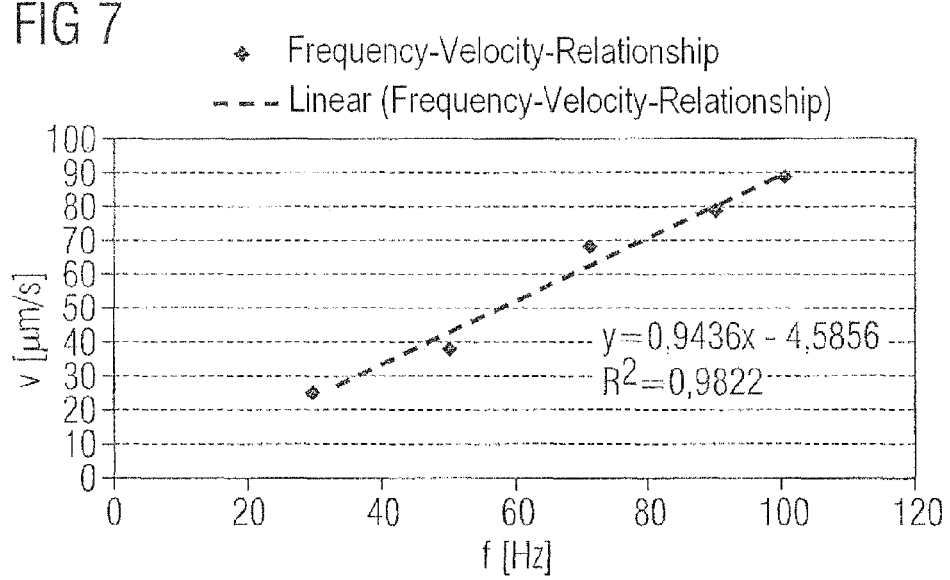

In FIG. 7 a relationship between repetition rate f in Hz and the cutting speed v in μm/s is shown. Here again a linear relationship of the form v=a·f+b results, a and b again being parameters which may be stored. Also this relationship may be used in the previously discussed embodiments.

Figure 8:
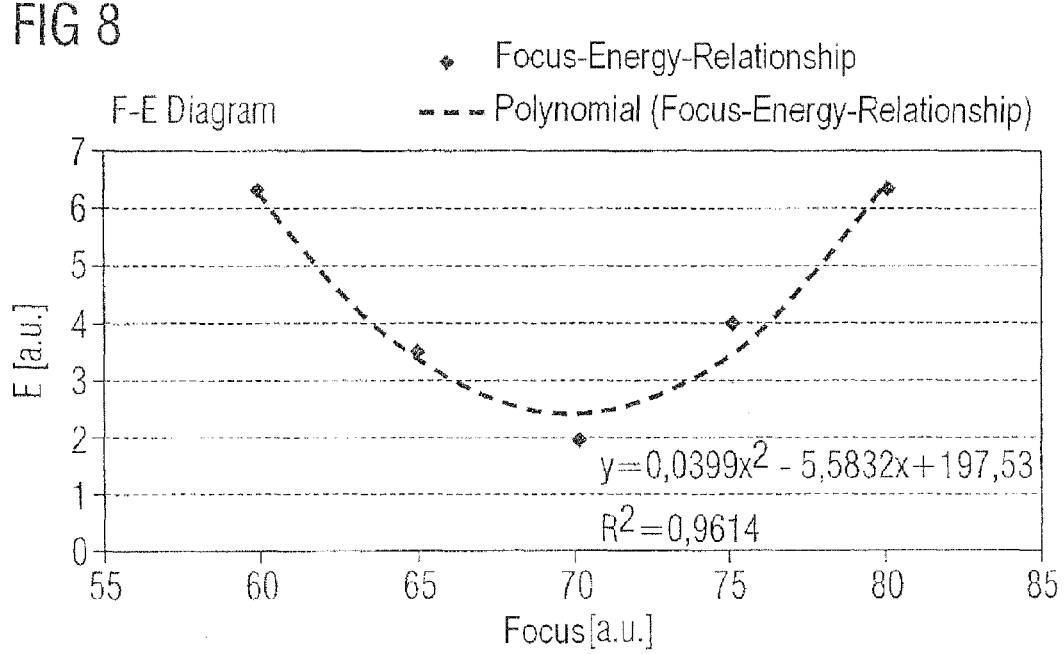

Finally, in FIG. 8 a relationship between laser focus and pulse energy is shown. When recording the curve shown in FIG. 8 at focus 70 a cut quality was at an optimum. Subsequently, the laser focus was varied, whereby at least to some extent a change of the focus may be compensated by increasing the laser energy, which in this case may lead to a wider cut, but may nevertheless ensure an interruption-free cut line. Therefore, in principle also this relationship which in the example shown is a quadratic relationship of the form e=a·Focus²+b·Focus+c, a, b and c being parameters, may be used.

FIGS. 5-8 are to be understood merely as examples that different system parameters may mutually compensate each other for reaching equal or similar cut lines, i.e. equally or similar cut line parameters. Curves as shown in FIGS. 5-8 as already mentioned may be recorded via a calibration and for example be stored in the form of corresponding fit parameters like the above-mentioned parameters a, b and c or also in the form of look-up tables in which fixed values are stored. The adjustment of system parameters as described may then take place depending on the thus stored characteristic curve. Such recordings may be done for different kinds of samples or sample carriers, respectively. Apart from the parameters shown in FIGS. 5-8 also other parameters like laser aperture or laser profile, for example a beam form may be varied. Furthermore, instead of the cut line parameters according to which a cutting just takes place without interruptions for example also a cut line parameter which indicates a cut width may be kept constant. As apparent from the above explanations of diverse modifications and variations the invention is not limited to the embodiments shown. These therefore are not to be construed as limiting.

The invention claimed is:

1. A method for laser microdissection, comprising:
adjusting at least one first system parameter of a laser microdissection system, and
automatically adjusting at least one second system parameter of the laser microdissection system depending on the at least one first system parameter such that a desired value of a cut line parameter describing a cut line of the laser microdissection is present;
wherein the cut line parameter is selected from the group comprising a cut width and a parameter describing an interruption freeness of the cut line.

2. The method of claim 1, further comprising:
initial adjusting of the at least one first system parameter and the at least one second system parameter such that the desired value of the cut line parameter is present,
wherein adjusting of the at least one first system parameter comprises a varying of the at least one first system parameter from a value of the initial adjusting, and
wherein the automatic adjustment of the at least one second system parameter takes place such that the desired cut line parameter is kept constant at least within a predetermined range.

3. The method of claim 2, further comprising a confirming of the cut line parameter as to be kept to be constant after the initial adjusting.

4. The method of claim 2, further comprising using a slower cutting speed in conjunction with the initial adjusting, and then using a higher cutting speed for actual cutting of the sample.

5. The method of claim 1, further comprising cutting of a biologic object with the at least one first system parameter and the at least one second system parameter.

6. The method of claim 1, wherein the at least one first system parameter is selected from a group comprising an energy of a laser, a repetition rate of a laser, a focus of a laser, an aperture of a laser, a profile of a laser beam of a laser and a cutting speed.

7. The method of claim 1, wherein the at least one second parameter is selected from a group comprising an energy of a laser, a repetition rate of a laser, a focus of a laser, an aperture of a laser, a profile of a laser beam of a laser and a cutting speed.

8. The method of claim 1, wherein the automatically adjusting takes place depending on at least one characteristic curve, which describes a dependency of the at least one second parameter from the at least one first system parameter with at least one predetermined cut line parameter.

9. The method of claim 1, wherein the adjusting of the at least one first system parameter comprising an adjusting of a laser energy and/or a repetition rate of a laser, and wherein the automatic adjusting of at least one second parameter comprises an adjusting of the cutting speed such that a resulting cut line is free of interruptions.

10. The method of claim 1, wherein adjusting of the at least one first system parameter comprises an increasing of a cutting speed.

11. The method of claim 1, wherein the adjusting of the at least one first system parameter is performed by a user of the laser microdissection system.

12. A laser microdissection system, comprising:
a laser device,
a receiving device for a sample to be treated, and
a control device, wherein the control device is configured to enable an adjusting of at least one first system parameter of the laser microdissection system and further to automatically adjust at least one second system parameter of the laser microdissection system depending on the at least one first system parameter such that a desired value of a cut line parameter describing a cut line of the laser microdissection system is obtained;
wherein the cut line parameter describes an interruption freeness of the cut line.

13. The system of claim 12, further comprising a user interface for adjusting the at least one first system parameter.

14. The system of claim 12, the system being configured to allow:
an initial adjusting of the at least one first system parameter and the at least one second system parameter such that the desired value of the cut line parameter is present,
wherein adjusting of the at least one first system parameter comprises a varying of the at least one first system parameter from a value of the initial adjusting, and
wherein the control device is configured such that the automatic adjustment of the at least one second system parameter takes place such that the desired cut line parameter is kept constant at least within a predetermined range.

15. The system of claim 12, wherein the control device is configured such that the automatically adjusting takes place depending on at least one characteristic curve, which describes a dependency of the at least one second parameter from the at least one first system parameter with at least one predetermined cut line parameter.

16. The system of claim 12, wherein the at least one first system parameter is selected from a group consisting of an energy of a laser, a repetition rate of a laser, a focus of a laser, an aperture of a laser, a profile of a laser beam of a laser and a cutting speed.

17. The system of claim 12, wherein the at least one second parameter is selected from a group consisting of an energy of a laser, a repetition rate of a laser, a focus of a laser, an aperture of a laser, a profile of a laser beam of a laser and a cutting speed.

18. The system of claim 12, wherein the control device is configured to adjust at least one of a laser energy and a repetition rate as adjustment of the at least one second system parameter in response to an increasing of a cutting speed as the adjusting of the at least one first system parameter.

19. A laser microdissection system, comprising:
a laser device,
a receiving device for a sample to be treated, and
a control device, wherein the control device is configured to enable an adjusting of at least one first system parameter of the laser microdissection system and further to automatically adjust at least one second system parameter of the laser microdissection system depending on the at least one first system parameter such that a desired value of a cut line parameter describing a cut line of the laser microdissection system is obtained;
wherein the cut line parameter is the cut width of the cut line.

* * * * *